United States Patent [19]
Opolski

[11] Patent Number: 6,096,726
[45] Date of Patent: Aug. 1, 2000

[54] MULTICOMPONENT COMPLEX FOR USE WITH SUBSTRATE

[75] Inventor: Margaret P. Opolski, Carlisle, Mass.

[73] Assignee: Surface Solutions Laboratories Incorporated, Carlisle, Mass.

[21] Appl. No.: 09/038,340

[22] Filed: Mar. 11, 1998

[51] Int. Cl.[7] .............................. A01N 43/04; A61J 3/00; B01J 13/00; A61L 5/103
[52] U.S. Cl. ............................ 514/53; 427/2.1; 427/2.14
[58] Field of Search ................................ 514/53; 427/2.1, 427/2.14

[56] References Cited

U.S. PATENT DOCUMENTS 5,702,754  12/1997  Zhong ..................................... 427/2.12

FOREIGN PATENT DOCUMENTS

| | | |
|---|---|---|
| 0728487 | 8/1996 | European Pat. Off. ........ A61L 29/00 |
| WO 90/05018 | 5/1990 | WIPO . |
| WO 94 27641 | 12/1994 | WIPO . |

OTHER PUBLICATIONS

Song, Cunxian et al., "Functional poly(.epsilon.–caprolactone)/polyether block copolymers as hemocompatible matrix for protein release", Proc. Int. Symp. Controlled Release Bioact. Mater. (1997), 24th, 465–476, XP002111230 (Figure 1).

Van Delden, C.J. et al., "Heparinization of gas plasma–modified polystyrene surfaces and the interactions of these surfaces with proteins studied with surface plasmon resonance", Biomaterials (1997), 18(12), 845–852, XP002111231.

Database WPI, Section Ch, Week 7932, Derwent Publications Ltd., London, GB; Class A23, AN 79–58650B, XP002111232 & JP 54 079997 A (Unitika Ltd.), Jun. 26, 1979, Abstract.

Database WPI, Section Ch, Week 7715, Derwent Publications Ltd., London, GB; Class A23, AN 77–26254Y, XP002111233 & JP 52 028596 A (Unitika Ltd.), Mar. 3, 1977, Abstract.

*Primary Examiner*—Avis M. Davenport
*Attorney, Agent, or Firm*—Hamilton, Brook, Smith & Reynolds, P.C.

[57] ABSTRACT

Compositions and methods for use with substrates which are useful in the sustained delivery of bioeffecting agents are described. The compositions of the invention include a multicomponent complex which attaches a bioeffecting agent to a substrate with an anchor provided by a linker compound which also forms a cleavable linkage so that the bioeffecting agent's release into the area surrounding the substrate occurs in a sustained manner over an extended period of time. The methods of the invention involve providing a bioeffecting composition on the surface of a substrate so that a bioeffecting agent may be released in a sustained manner over time.

66 Claims, 10 Drawing Sheets

MULTICOMPONENT COMPLEX FOR USE WITH SUBSTRATE

BACKGROUND

Bioeffecting agents—agents which engage in a biological activity or are effective in modulating a biological activity—are often applied to the surface of articles for a variety of purposes. For example, bath mats are often sprayed with agents containing benzylammonium salts to inhibit the growth of microbes. Bioeffecting agents are also used to alter the surface properties of the materials to which they are applied. A pharmaceutical preparation of heparin when applied to a medical device provides its surfaces with antithrombogenic properties.

To prolong the duration of the bioeffecting activity or to delay its initiation, bioeffecting agents have been encapsulated or embedded in materials for subsequent release in particular locations or under particular conditions. For example, polyglycolic and polylactic acids have found significant usage as resorbable biomaterials and have often been blended during processing to include a variety of bioeffecting agents. The bioeffecting agents contained in these materials are released as the products degrade. The rate of delivery of the agents is determined by the local conditions which affect the diffusion of the bioeffecting agents and the degradation of the enclosing materials. Bioeffecting agents have also been incorporated in materials such as hydrogels which swell in moist environments. Hydrogels release the agents through diffusion into the local environment.

Various types of chemical attachments have been employed to bind bioeffecting agents to articles in attempts to improve the duration of the bioeffecting activity. A number of ionic bonds have been used, because bioeffecting agents possessing sufficient ionic charge can be readily attached to the surfaces of articles containing the opposite ionic charge. Hsu, for example, in U.S. Pat. No. 4,871,357, describes an ionic heparin coating for use with medical devices. The release of materials which are attached to substrates with ionic bonds is governed both by the strength and number of the ionic pairs, and by local conditions such as pH and moisture. Ionic bonds disassociate quite rapidly under moist conditions. Even ionic systems of attachment designed to include protectants against wet environments tend to be less durable under those conditions. Ionic attachment can also adversely affect the function of bioaffecting materials during the period of attachment.

Covalent bonds, relying on a number of functional groups, have been used to attach bioeffecting agents to the surface of articles. In U.S. Pat. No. 4,810,784, Larm described a method of covalent attachment using glutaraldehyde and aldehyde conversions, while Burns utilized a method of attachment relying on carbodiimide conversion in U.S. Pat. No. 5,527,893. Guire, in U.S. Pat. No. 5,336,579, described a method which used a combination isocyanate and photo-activation hydrogen abstraction. While these types of bonds provide good attachment of the agent to the article, they can be difficult and complicated to form on the surface of the substrate, often requiring multiple modifications. In addition, the final covalent bond formed is not generally reversible, and the bioaffecting activity of the agent is often altered significantly by its interaction with the functional group providing the attachment.

SUMMARY OF THE INVENTION

The present invention is based, at least in part, on the discovery of a multicomponent complex for reversibly attaching bioeffecting agents to substrates so that the agents may be released over an extended period of time while still retaining the capacity for substantial bioeffecting activity. The invention provides compositions and methods for use with substrates which are useful in the sustained delivery of bioeffecting agents. The compositions of the invention include a multicomponent complex which attaches a bioeffecting agent to a substrate with an anchor provided by a linker compound which also forms a cleavable linkage so that the bioeffecting agent's release into the area surrounding the substrate occurs in a sustained manner over an extended period of time. The methods of the invention involve providing a bioeffecting composition on the surface of a substrate so that a bioeffecting agent may be released in a sustained manner over time. Accordingly, the compositions and methods of the invention are useful for delivering bioeffecting agents to a localized area where their sustained release permits bioeffecting activity to occur over an extended period of time.

The present invention pertains to a combination of a multicomponent complex for delivering a bioeffecting agent for use with a substrate and an article. The combination includes a complex for delivering a bioeffecting agent for use with a substrate and for delivering a bioeffecting agent having a bioeffecting domain component, a segment component containing at least two linking domains, and an anchoring moiety component. Accordingly, the multicomponent complex can have the formula:

[Q]-[S]-[T]

where Q is a bioeffecting domain component; S is a segment component containing at least two linking domains; and T is an anchoring moiety component; and the components are selected such that a cleavable linkage anchored to the substrate is formed which sustains the release of the bioeffecting agent over time. The combination contains an article which is in contact with the complex. In one preferred embodiment, the article is a medical device adapted for in vivo uses.

The present invention also provides a multicomponent complex for delivering a bioeffecting agent for use with a substrate having a bioeffecting domain component, a segment component containing at least two linking domains, and an anchoring moiety component. Accordingly, the multicomponent complex can have the formula:

[Q]-[S]-[T]

where Q is a bioeffecting domain component; S is a segment component containing at least two linking domains; and T is an anchoring moiety component and the components are selected such that a cleavable linkage anchored to the substrate is formed which sustains the release of the bioeffecting agent over time.

The present invention also provides a composition for delivering a bioeffecting agent for use with a substrate. The composition contains a multicomponent complex for delivering a bioeffecting agent for use with a substrate having a bioeffecting domain component, a segment component containing at least two linking domains, and an anchoring moiety component. Accordingly, the multicomponent complex can have the formula:

[Q]-[S]-[T]

where Q is a bioeffecting domain component; S is a segment component containing at least two linking domains; and T is an anchoring moiety component and the components are selected such that a cleavable linkage anchored to the substrate is formed which sustains the release of the bioeffecting agent over time. The composition contains a solution in contact with the complex.

The present invention further pertains to packaged compositions for delivering a bioeffecting agent for use with a substrate. A packaged composition includes a container holding a compound supplying at least one component of a multicomponent complex for delivering a bioeffecting agent for use with a substrate having a bioeffecting domain component, a segment component containing at least two linking domains, and an anchoring moiety component. Accordingly, the multicomponent complex can have the formula:

[Q]-[S]-[T]

where Q is a bioeffecting domain component; S is a segment component containing at least two linking domains; and T is an anchoring moiety component and the components are selected such that a cleavable linkage anchored to the substrate is formed which sustains the release of the bioeffecting, agent over time. The packaged composition contains instructions for using the composition to deliver a bioeffecting compound.

The present invention also provides methods for providing a sustained release bioeffecting coating on the surface of an article by applying a coating solution to a surface of the article such that a layer containing the sustained release bioeffecting coating is formed upon the article surface, such that the formed layer contains a multicomponent complex containing a bioeffecting domain component, a segment component containing at least two linking domains, and an anchoring moiety component, the components selected such that a cleavable linkage anchored to the substrate is formed, and the release of the bioeffecting domain is sustained over time.

DETAILED DESCRIPTION

Figure 1:
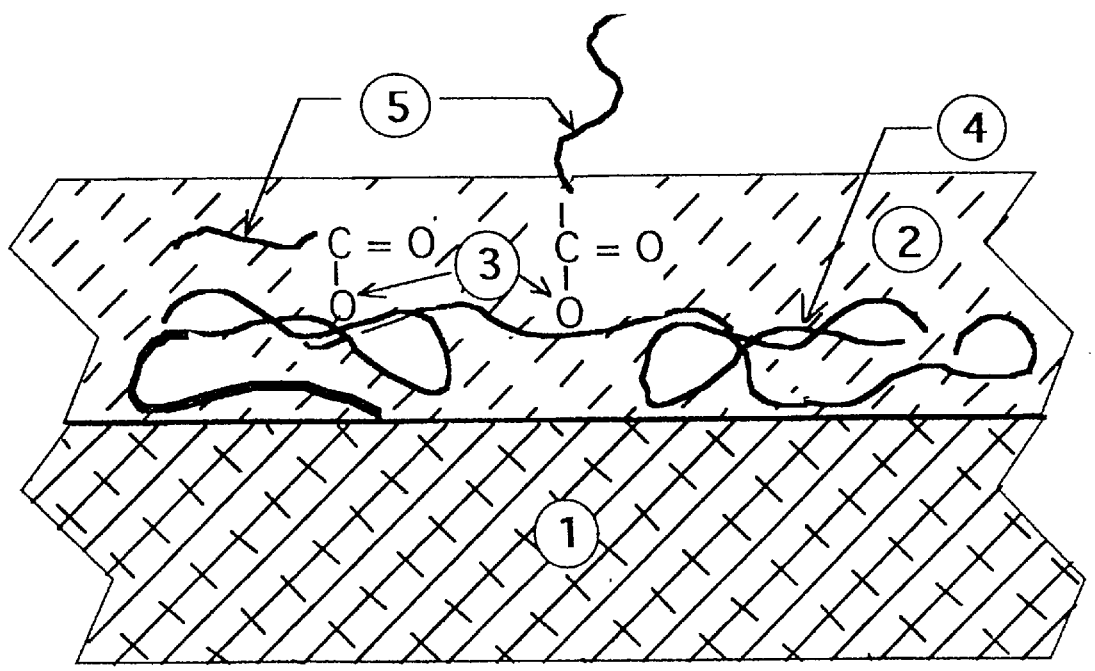
FIG. 1 is an illustration of a one-step method of application of a multicomponent complex of the invention.
Figure 2:
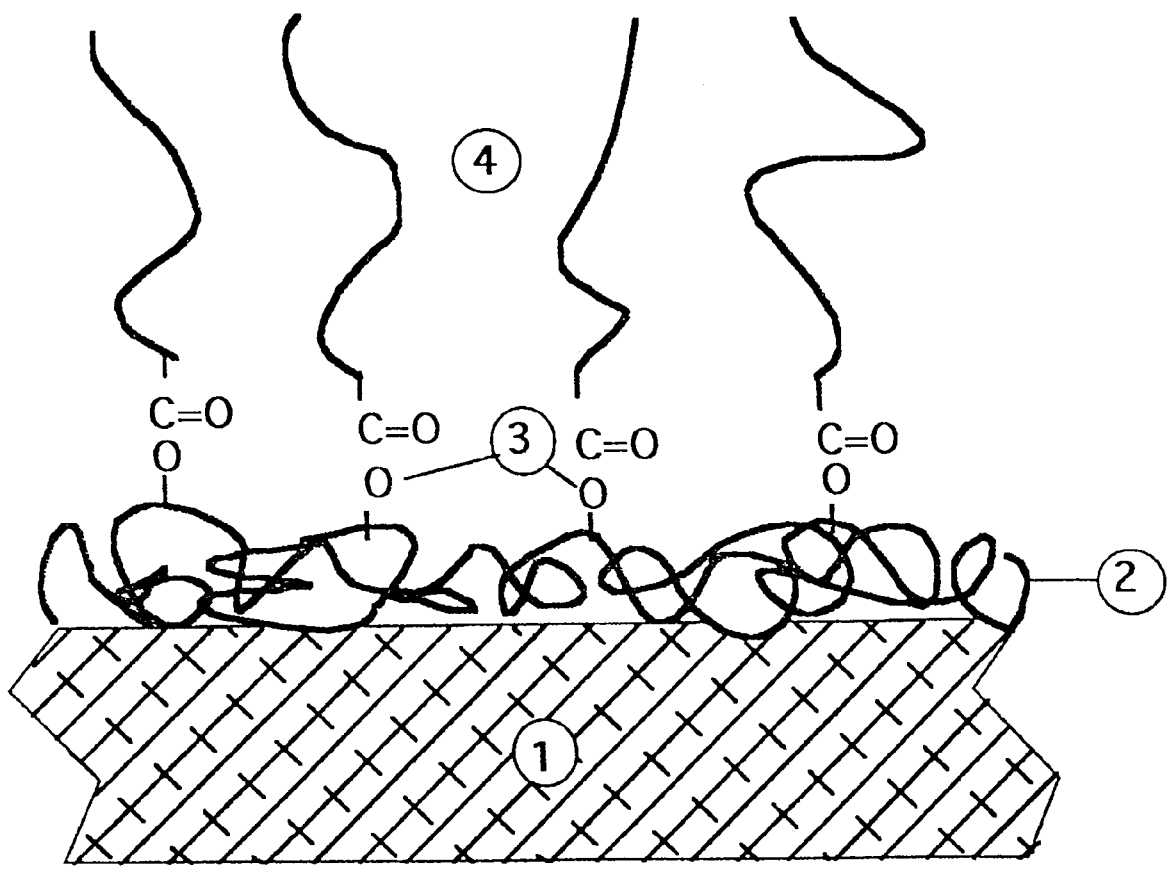
FIG. 2 is an illustration of a two-step method of application of a multicomponent complex of the invention.

The features and other details of the invention will be particularly described and pointed out in the claims. It will be understood that the particular embodiments of the invention are shown by illustration and not as limitations of the invention. The principal features of the invention can be employed in various embodiments without departing from the scope of the present invention. All parts and percentages are by weight unless otherwise stated.

The present invention pertains to compositions and methods useful in the delivery of bioeffecting agents. The compositions of the invention include a multicomponent complex which attaches a bioeffecting agent to a substrate with an anchor provided by a linker compound which also forms a cleavable linkage with the bioeffecting agent so that the bioeffecting agent's release into the area surrounding the substrate occurs in a sustained manner over an extended period of time. The present invention also pertains to methods for providing a sustained release bioeffecting coating on the surface of an article by applying a coating solution to a surface of the article.

The language "multicomponent complex" in intended to include the multicomponent complexes of the invention that attach a bioeffecting agent to a substrate using a cleavable linkage and an anchor. The components forming the multicomponent complex are selected to form a cleavable linkage and and an anchor such that the release of the bioeffecting agent is sustained over time. The bioeffecting domain component is supplied by a bioeffecting agent. The segment component containing at least two linking domains is supplied by a linker compound. The anchoring moiety component is associated with the substrate, and may be supplied by the substrate or another compound placed in close proximity to the substrate.

Accordingly, the multicomponent complex of the invention can have the formula:

[Q]-[S]-[T]

wherein Q is a bioeffecting domain component; S is a segment component containing at least two linking domains; and T is an anchoring moiety component.

The language "bioeffecting agent" is intended to include a material which engages in biological activity or is effective in modulating a biological activity. A bioeffecting agent may exhibit therapeutic, prophylactic or diagnostic effects in humans, animals, insects and plants. Agents may be proteins, peptides, polysaccharides, enzymes, drugs, vaccines, vitamins, mineral complexes, sunscreens or nutritional supplements. Preferred materials exhibit antithrombogenic, antimicrobial, antihypertensive, anticarcinogenic, anticonvulsive, antiinflammatory, analgesic, antifibrotic, cell growth or cell inhibition, or other properties. Agents may be used to treat a variety of disease states including Parkinson's Disease, Alzheimer's Disease, and any form of diabetes. Preferred materials include ferrochorome A, erythropoietin, growth hormone, insulin, vitamin C, aspirin and heparin. Particularly preferred materials are anticoagulant compounds and proteins which affect cell growth in humans. A most particularly preferred compound is ammonium heparin.

Bioeffecting agents useful in the multicomponent complex of the invention are those that contain at least one localized site useful as a bioeffecting domain component. The site may either be naturally contained in the agent, or the agent may be modified to contain the site. Materials modified before, during or after their use in the multicomponent complex of the invention are included in the language bioaffecting agents as long as they maintain a substantial capacity to engage in biological activity or maintain a substantial effectiveness in modulating a biological activity. The language "a substantial capacity to engage in biological activity" or "a substantial effectiveness in modulating a biological activity" is considered to be activity that is at least about 10% of the activity of the unmodified agent, preferably at least about 20% of the activity of the unmodified agent, most preferably at least about 30% of the activity of the unmodified agent. Materials which, as modified, fail to maintain a substantial capacity to engage in biological activity or to maintain a substantial effectiveness in modulating a biological activity, may be subsequently modified to regain a substantial capacity to engage in biological activity or regain a substantial effectiveness in modulating a biological activity e.g., an agent which fails to maintain a substantial capacity to engage in biological activity when attached to a substrate with a multicomponent complex of the invention, but regains a sustantial capacity to engage in biological activity when released from the multicomponent complex is intended to be included in the language, bioeffecting agent.

The language "bioeffecting domain component" is intended to include a localized site located on a bioeffecting agent. The language "supplied by" is intended to include the use of a bioeffecting domain component contained on a bioeffecting agent in a multicomponent complex of the invention. The bioeffecting domain component is considered to be supplied by the bioeffecting agent on which it is contained. The bioeffecting domain component is capable of forming a cleavable linkage when combined with a linking domain contained in a linker compound. A site which forms an appropriate covalent chemical bond may be utilized. Preferred sites are acid functional sites containing a carboxylic acid (COOH).

Bioeffecting agents may naturally contain a bioeffecting domain component. A preferred bioaffecting agent with a naturally occurring bioeffecting domain component is ammonium heparin. Bioaffecting agents may be modified to contain a bioeffecting domain component by chemically reacting the bioeffecting agent with an appropriate carboxylic acid reactive species. A carboxy modified isocyanate is one example of an appropriate carboxylic acid reactive species, which use is described in Example 8.

Table 1 below contains a non-limiting list of examples of bioeffecting agents and a corresponding bioeffective domain component they may contain. The table also contains the names of commerical distributors of bioeffecting agents.

TABLE 1

COMPOUNDS, DISTRIBUTORS AND DOMAINS OF BIOEFFECTING AGENTS

| Name | Supplier(s) | Domain |
|---|---|---|
| Antithrombogenic Properties: | | |
| heparin | Various | —COOH |
| dermatan sulfate | Various | |
| Cell Growth Properties: | | |
| ferrochrome A | | —COOH |
| erythropoetins | | —COOH |
| diethylstilbestrol | | —OH |
| Lupron | | —NH2/—OH |
| Estrogen Estradiol | | —OH |
| Androgen Halotestin | Pharmacia/Upjohn | —OH |

TABLE 1-continued

COMPOUNDS, DISTRIBUTORS AND DOMAINS OF BIOEFFECTING AGENTS

| Name | Supplier(s) | Domain |
|---|---|---|
| Anticarcinogenic Properties: | | |
| 6-thioguanine | Glaxo Wellcome | —COOH |
| 6-mercaptopurine | Glaxo Wellcome | —COOH |
| Zolodex | | —NH2/—OH |
| Taxol | | —OH |
| Antihypertensive Properties: | | |
| Lisinopril/Zestril | Zeneca | COOH |
| Streptokinase | | COOH |
| aminobutyric acid | | OH |
| hemostatic aminocaproic acid | | COOH |
| Parkinson Treatment: | | |
| Parlodel | Sandoz | OH |
| Alzheimer's Treatment | | |
| Tacrine Hcl | ParkeDavis | NH2 |
| Antifibrosis | | |
| Potaba | Glenwood Pharmaceuticals | NH2 |
| Appetite Control Properties: | | |
| Adipex | Gate Pharmaceuticals | —NH2 |
| Anticonvulsive Properties: | | |
| Memboral | Sanofi-Winthrop | —COOH |
| Phenobarbital | Various | —2ON |
| Diabetes Mellitus Treatment: | | |
| Insulin | Various | —COOH/NH2 |
| Proteins: | | |
| gamma globulin | | —COOH/NH2 |
| azathioprine | | |
| Enzymes: | | |
| papein | | —COOH/NH2 |
| Antiinflammatory/Analgesic Properties: | | |
| acetaminophen | Various | —OH/2ON |
| ibuprofen | Various | —COOH |
| acetylsalicylic acid derivatives | Salflex-Carnick Labs | —COOH |
| epinephrine | Various | —OH |
| hydrocortisone | Various | —OH |
| Oxycodone Percoset | Dupont | —OH |
| Dalgan | Astra | —OH |
| Phreniline butabital | Carnick Labs | —2ON |
| Procaine (topical) | | —NH2 |
| Novocain | Sonofi-Winthrop | |
| Vitamin/Mineral complexes: | | |
| hemin | | —COOH |
| vitamin B-12 | | —COOH |
| folic acid | | —COOH |
| magnesium gluconate | | —COOH |
| vitamin D | | —OH |
| vitamin C | | —COOH |
| vitamin E | | —OH |
| vitamin A | | —OH |
| vitamin U | | |
| vitamin L | | —NH2 |
| vitamin K | | —OH/NH2 |
| pantothenic acid | | —COOH |
| Ultraviolet Light Inhibitors: | | |
| para-aminobenzoicacid | | —COOH |
| Rodenticides: | | |
| aminopterin | | —NH2 |
| Muscle Relaxant Properties: | | |
| aminophenylbutyric acid | | —COOH |

TABLE 1-continued

COMPOUNDS, DISTRIBUTORS AND DOMAINS OF BIOEFFECTING AGENTS

| Name | Supplier(s) | Domain |
| --- | --- | --- |
| Vaccines/Vaccine Adjuvants: | | |
| hepatitis | | —COOH/NH2 |
| chicken pox | | —COOH/NH2 |
| measles | | —COOH/NH2 |
| diptheria | | —COOH/NH2 |
| antithemophilic | | —COOH/NH2 |
| Bayer's Koate | | —COOH/NH2 |
| Antimicrobial Properties: | | |
| penicillin | Various | —COOH |
| Acyclovir | Glaxo Wellcome | —COOH/NH2 |
| oflaxacin | McNeil | —COOH |
| Amoxicillin | | —COOH |
| Tobramycin | | —NH2 |
| Retrovior | | —NH2 |
| Epivir | | —2ON |
| Nevirapine | Roxane | |
| Gentamycin | Schering Plough | —NH2 |
| Duracef | | —COOH |
| Ablecet | Eli Lilly | COOH |

The language "substrate" is intended to include a material which can be used with the multicomponent complex. Substrates useful with the invention are those associated with an anchoring moiety component. The language "associated with an anchoring moiety component" is intended to include substrates which naturally contain at least one anchoring moiety component, substrates which may be modified to contain at least one anchoring moiety component, and substates to which materials may be applied which contain at least one anchoring moiety component. Useful substrates include a variety of solid, semi-solid and gelled materials. Preferred substrates include metals and polymers. Particularly preferred substrates are steel and urethane.

In certain embodiments of the invention, the substrate is not formed into an article. For example, the components of the multicomponent complex of the invention can be added to a bulk material before it is formed into an article. However, in certain embodiments of the invention, particularly those in which a substrate is used to deliver a bioeffecting agent in vivo in humans or animals, the substrate is formed into an article. These articles will often be medical devices. The language "medical device" is intended to include an article regulated under the United States Federal Food, Drug and Cosmetic Act as a medical device. Preferred medical devices include catheters, stents and a variety of medical implants intended for used in humans. These articles vary in size and shape but are at least about a few tenths of a millimeter long and weigh at least about a few milligrams. Such articles are formed of a variety of substrates. Preferred substrates for these embodiments are metals and polymers. Particularly preferred embodiments are steel and urethanes.

The language "cleavable linkage" is intended to include those covalent chemical bonds which attach bioeffecting agents to substrates in a manner such that when disassociation occurs, and the bioeffecting materials are released, the bioeffecting activity of the bioeffecting materials is substantially maintained. Covalent bonds which are disassociated by hydrolyis reactions are preferred. Covalent bonds which result in the formation of esters are particularly preferred.

The language "reversibly attached" is intended to include the manner in which a bioeffecting agent is attached to a substrate with a "cleavable linkage" of the invention.

The language "supplied by" is intended to include the use of a linking domain contained on a segment component of a linker compound in a multicomponent complex of the invention. The language "segment component" is intended to include a portion of a linker compound which contains a linking domain. A segment component is considered to be supplied by a linker compound. A linking domain is also considered to be supplied by a linker compound.

The language "linking domain" is intended to include a localized site on a segment component of a linker compound which when combined with a bioeffecting domain component forms a cleavable linkage. A site which forms an appropriate covalent chemical bond may be utilized. Preferred sites are acid reactive sites containing carboxylic acids. Particularly preferred sites are acid reactive sites containing un-neutralized or fugitive counter-ion carboxylic acids.

The language "linking domain" is also intended to include a localized site on a segment component of a linker compound which when combined with an anchoring moiety component forms an anchor.

Table 2 below contains a non-limiting list of compounds which can supply linking domains. The table also contains the names of commerical distributors of linker compounds.

TABLE 2

COMPOUNDS AND DISTRIBUTORS OF LINKING AGENTS

| Name/Type | Supplier(s) |
| --- | --- |
| aziridine (polyfunctional) | Various including: |
| | Stahl Chemical, Peabody, MA |
| epoxies (polyfunctional) | Dow Chemical, Midland, MI |
| epoxy function silanes | OSI Specialty Chemical, Danbury, CT |
| | Shell Chemical, Houston, TX |
| | Henkel Corp. |
| | Dupont, Wilmington, DE |
| titanate | Dupont, Wilmington, DE |
| zirconate | Kenrich |
| zircoaluminate | Chartwell |
| formaldehyde (derivatives) | Cytec, NJ |
| ureaformaldehyde condensates | Solutia, St. Louis, MO |
| melamine formaldehyde condensates | |
| glycouril | |
| benzoguanamine | |

The language "anchoring moiety component" is intended to include a localized site capable of reacting with a linking domain to form an anchor. The language "anchor" is intended to include a chemical bond that attaches the segment component to the substrate or to a material applied to the substrate. An anchor may be an ionic or a covalent chemical bond. Preferred chemical bonds include urethane, urea, amide, ether, ester, siloxy, alkyl, metal esters, and melamine bonds. The language "supplied by" is intended to include the use of a linking domain contained on a segment component in a multicomponent complex of the invention. The anchoring moiety component is considered to be supplied by the substrate or a material applied to the substrate.

An anchoring moiety may be a naturally occurring site located on a substrate used with the multicomponent complex. Alternately, a substrate used with a multicomponent complex of the invention may be modified to contain an anchoring moiety. A substrate may be modified to contain an anchoring moiety by a method known in the art. Examples of methods known in the art include flame treatment, plasma treatment, treatment with ultraviolet or high energy radiation, acid treatment, corona discharge, gas plasma, treatment with various primers, and copolymerization with functional monomers.

Alternately, an anchoring moiety may be contained in a material applied to a surface of a substrate used with a multicomponent complex of the invention. The material supplying the anchoring moiety may be applied to the surface of the substrate in a solution separate from a solution containing the multicomponent complex. Alternately, the material supplying the anchoring moiety may be mixed with a solution containing the multicomponent complex.

Table 3 below contains a non-limiting list of materials which can supply anchoring moieties. The table also contains the names of commerical distributors of the materials.

TABLE 3

COMPOUNDS AND SUPPLIERS OF MATERIALS PROVIDING ANCHORING DOMAINS

| Name/Type | Supplier(s) |
|---|---|
| acrylic (emulsion polymers containing some AA or MAA) | Various including: Zeneca Resins, Wilmington MA Stahl Chemical, Peabody, MA BF Goodrich, Leominster MA and Cleveland OH Rohm and Haas, Philadelphia PA |
| urethane | Zeneca Resins, Wilmington MA Stahl Chemical, Peabody, MA BF Goodrich, Leominster MA and Cleveland OH Bayer Corporation, Pittsburgh PA |
| alkyd | CCP Polymers, Kansas City MO |
| acrylic reactants | CCP Polymers Kansas City MO |
| polyesters | Eastman Chemical, Kingport, TN Akzo Nobel Resins, Louisville, CT |
| vinyl | Union Carbide Corporation, Danbury, CT |
| silicones | Tego Chemical, Hopewell, VA General Electric, Waterford, NY |
| nylon | Elf Atochem, Philadelphia, PA |
| epoxy | Shell Chemical, Houston, TX Ciba Henkel Corporation |
| synthetic rubbers (block copolymers) | BF Goodrich, Cleveland OH Dow Chemical, Midland, MI Air Products, Allentown, PA |
| acrylic acid polymers | Carbopol |
| maleic anhydride polymers | BF Goodrich, Cleveland OH |

The language "sustained release" is intended to include the release of a bioeffecting agent in a manner such that its appearance in a local environment is delayed and/or prolonged and its bioeffecting activity is therefore sustained in duration. Sustained release is measured by comparing the release of a bioaffecting agent attached to a substrate with the multicomponent complex of the present invention to the release of the bioaffecting agent attached to the same substrate by another means. Any measurable increase is considered to be a sustained release. At least about a two-fold increase is preferred. At least about a three-fold increase is particularly preferred. The duration of the sustained release will vary from time to time and depending on the actual conditions of use.

The release of bioaffecting agents attached to substrates with the multicomponent complex of the present invention is affected by, among other conditions, the combination of pH, moisture and temperature in the local environment in which it is used. Therefore, it is possible to control the amount of agent released into a local area over a period of time by adapting the manner in which the cleavable linkage attaches the agent to the substrate in relation to the pH, moisture content and the temperature in the area in which the substrate is utilized. The language "controlled release" is intended to include adaptations which permit a specific dose of a therapeutic bioeffecting agent to be released into a local environment for a specified period of time.

The language "di-functional spacer" is intended to include any material which is attached to the bioeffecting agent for the purpose of orienting its spatial arrangement in a particular manner. A di-functional spacer useful in the present invention contains at least one site which permits its attachment to the cleavable linkage or the anchor, or both sites of the multicomponent complex without significantly compromising the overall function of the complex. Examples of compounds useful as di-functional spacers include linear, end functional di-acid, acid/amine, acid/hydroxy, and acid/unsaturated materials. A preferred compound is aminocaprylic acid.

A composition containing the multicomponent complex can include additional compounds such as hydrophilic agents, some of which render the surface of the substrate slippery when placed in a moist environment. Some hydrophilic agents cause swelling which incorporates the bioeffecting agent into recesses formed on the surface of the substrate. The release of the bioeffecting agents can be further enhanced by the addition of hydrophilic agents which increase exposure of sensitive ester linkages to the environment.

Optionally, hydrophilic coreactants, which may be used in forming a polymer, may be added to the compound supplying the anchoring moiety. Such monomers as HEA, HEMA, VP, AA, NIPA can be added to form acrylic co-polymers. Hydroxy-terminal hydrophilic materials such as polyethylene oxide can be co-reacted to form esters, amides and urethanes to improve hydrophilicity.

Another aspect of the present invention includes a method in which the multicomponent complex is applied to at least one surface of a substrate. A solution containing the multicomponent complex may be applied to the surface of the substrate in a one-step application by dipping the substrate into the solution so that a single layer is formed on the surface of the substrate. The solution may contain additional ingredients such as hydrophilic polymers. Other methods of applying the coating are known to those skilled in the art and may be used in this application. One-step application methods are illustrated in FIGS. 1 and 4. In FIG. 1, #1 represents a surface of the substrate, #2 represents an optional hydrophilic polymer, #3 represents a cleavable linkage, #4 represents an anchor and #5 represents a bioaeffecting agent. In FIG. 4, #1 represents the surface of a substrate, #2 represents an optional primer layer, #3 represents an anchoring moiety, #4 represents a cleavable linkage and #5 represents a bioeffecting agent.

Alternately, the multicomponent complex may be applied to the surface of the substrate in a two-step application. A first primer layer containing a portion of the components necessary to form the multicomponent complex is applied to the surface of the substrate. Then, a second layer containing the remaining components necessary to form the multicomponent complex are applied over the primer layer. The multicomponent complex in this application is formed in situ. Either of the two solutions may contain additional ingredients such as hydrophilic polymers. Any method known to those of skill in the art may be used to apply the layers of the solutions to the substrate. Two-step application methods are illustrated in FIGS. 2 and 4. In FIG. 2, #1 represents a surface of the substrate, #2 represents a primer layer, #3 represents a cleavable linkage, #4 represents an anchor and #5 represents a bioeffecting agent. In FIG. 4, #1 represents a surface of the substrate, #2 represents an optional primer layer, #3 represents an anchoring moiety, #4 represents a cleavable linkage and #5 represents a bioeffecting agent.

Figure 3:
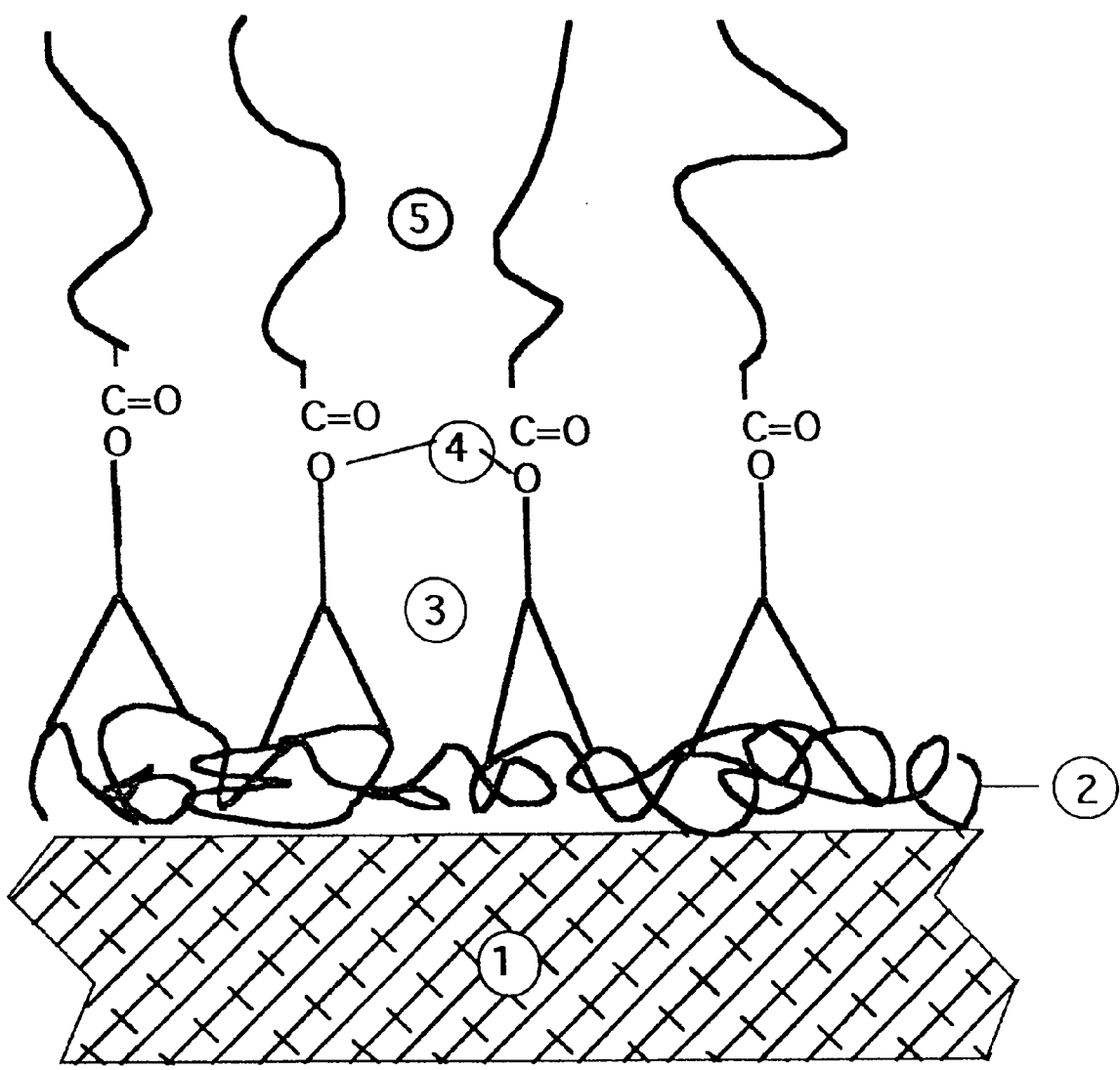
FIG. 3 is an illustration of a three-step method of application of a multicomponent complex of the invention.
Figure 4:
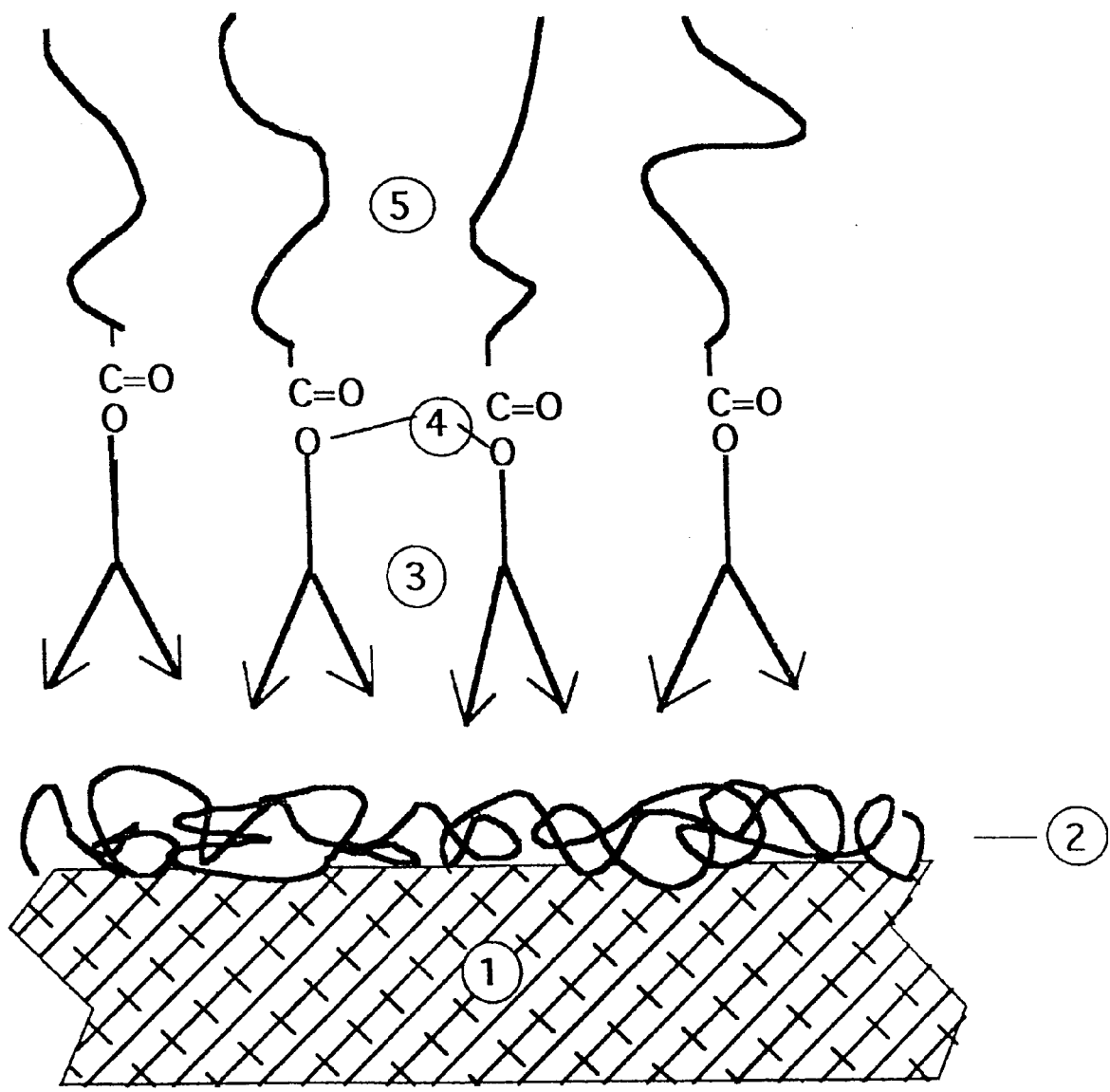
FIG. 4 is an illustration of a one-step or two-step method of application of a multicomponent complex of the invention.

Alternately, the multicomponent complex may be applied to the surface of the substrate in a three-step application A first primer layer containing a portion of the components necessary to form the multicomponent complex is applied to the surface of the substrate. Then, a second layer containing additional components necessary to form the multicomponent complex are applied over the primer layer. Finally, a third layer containing the remainder of the components necessary to form the multicomponent complex is applied over the first two layers. The multicomponent complex in this application is formed in situ. Any of the three solutions may contain additional ingredients such as hydrophilic polymers. Any method known to those of skill in the art may be used to apply the layers of the solutions to the substrate. This three-step application is illustrated in FIG. 3. In FIG. 3, #1 represents the surface of a substrate, #2 represents a primer layer, #3 represents a linker compound, #4 represents a cleavable linkage and #5 represents a bioeffecting agent.

Figure 5:
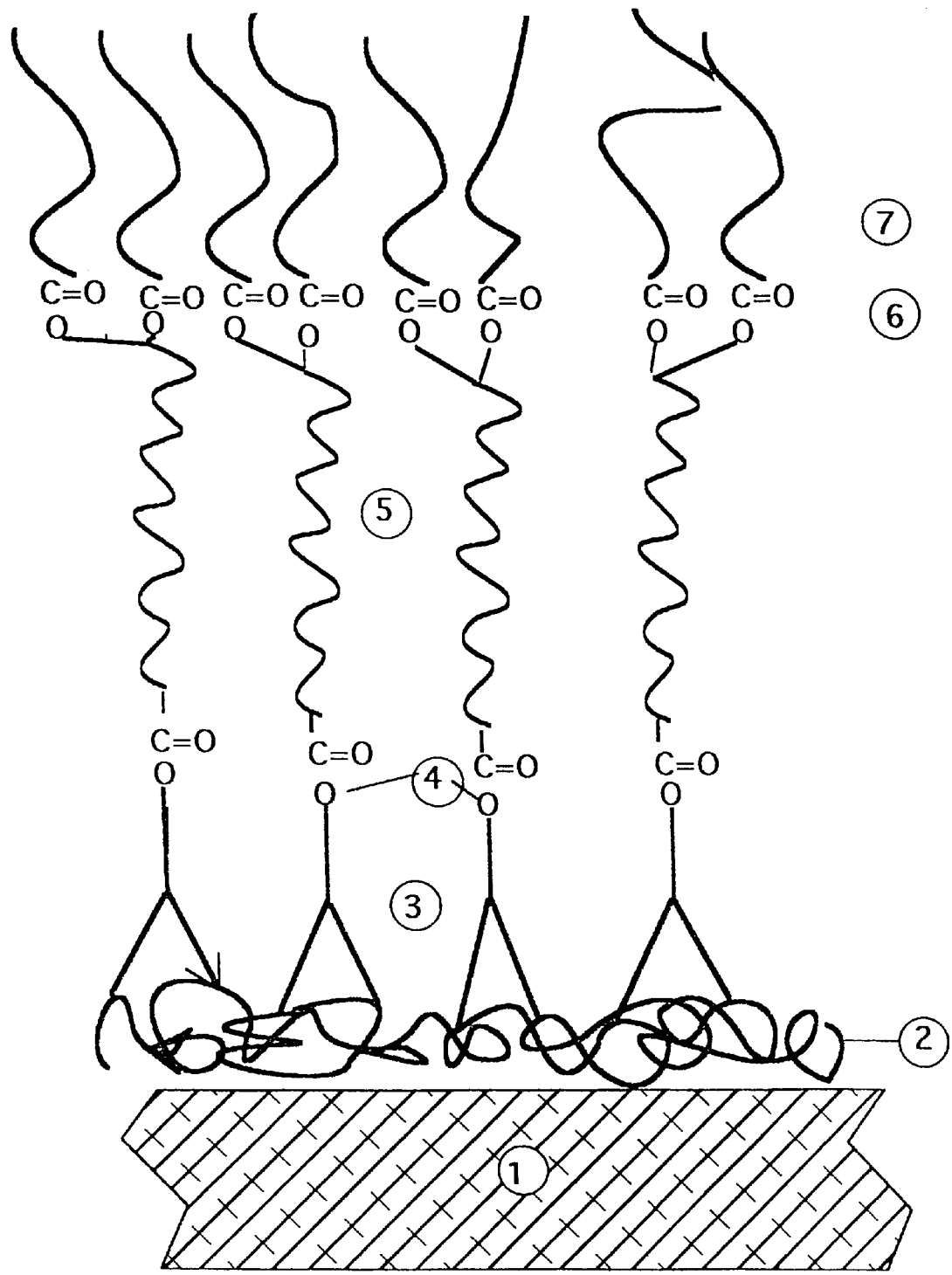
FIG. 5 is an illustration of a method of application of a multicomponent complex of the invention including a difunctional spacer.

In any of the applications described above, a di-functional spacer can be interspersed between the cleavable linkage and the anchor. For example, a first primer layer containing a portion of the components of the multicomponent complex is applied to the surface of the substrate. Successive layers containing a di-functional spacer and the remainder of the components of the multi-component complex are then applied. A method of application including a di-functional spacer is illustrated in FIG. 5. In FIG. 5, #1 represents a surface of the substrate, #2 represents an optional primer layer, #3 represents a linker compound, #4 represents a linkage of the di-functional spacer, #5 represents a di-functional spacer, #6 represents a cleavable linkage and #7 represents a bioeffecting agent.

In a preferred embodiment of the method of the present invention, a stainless steel substrate is coated by being dipped into a solution containing the multicomponent complex. The coating layer formed is preferably about one-tenth mil (0.1 mil) to ten mil (10.0 mil) in thickness, even more preferably three-tenths mil (0.3 mil) to five mil (5.0 mil) in thickness, most preferably about one mil (0.5 mil) to three mil (3.0 mil) in thickness. [Note: One mil equals 0.001 inch or 25.0 microns]

Another aspect of the present invention includes a method in which the components necessary for forming the multi-component complex are added into a substrate. Alternately, a solution containing the multi component complex can be added to the substrate.

In another aspect of the invention, the multicomponent complex is combined with an article in contact with the complex. The article sould be of a shape and formed of a material suitable for its purpose. In some embodiments, the articles are medical devices. Preferred medical devices include catheters, stents and a variety of implants. Such articles are formed of a variety of materials. Preferred materials for these embodiments are metals and polymers. These articles vary in size and shape but are at least about a few tenths of a millimeter long, preferably at least about 0. 1, 0.3, 0.5, 0.7 and 0.9, most preferably at least about 0.5, are at least about a few tenths of a millimeter in diameter, preferably at least about 0.1, 0.3, 0.5, most preferably at least about 0.3, and weigh at least about a few milligrams, preferably at least about 1.0, 3.0 and 5.0, most preferably at least about 3.0 milligrams.

In another aspect of the invention, the individual components of the multicomponent complex can be supplied in various configurations. Each compound necessary for forming the multicomponent complex of the invention, the compound supplying the bioeffecting domain, the compound supplying the linking segment component containing at least two domains and the compound supplying the anchoring moiety, can be provided in a container supplying at least one component. The language "supplying" when used to describe the manner in which the multicomponent complex is provided is intended to include provision of the multicomponent complex when the multicomponent complex is prepared and used in the same facility as well as when the multicomponent complex is prepared for use in separate facilities. The language "container" is intended to include any vessel or package capable of containing for any purpose or any period of time the multicomponent complex, any component of the multicomponent complex, or any compound or material intended to supply a component of the multicomponent complex.

In another embodiment, the compounds necessary for forming the multicomponent complex of the invention, the compound supplying the bioeffecting domain component, the compound supplying the segment component containing at least two linking domains and the compound supplying the anchoring moiety component, can be provided in a container holding compounds supplying at least two components.

In yet another embodiment, the compounds necessary for forming the multicomponent complex of the invention, the compound supplying the bioeffecting domain component, the compound supplying the segment component containing at least two linking domains and the compound supplying the anchoring moiety component, can be provided in a container holding compounds supplying at least three components.

In another aspect of the invention, at least one of the compounds necessary for forming the multicomponent complex of the invention, the compound supplying the bioeffecting domain component, the compound supplying the segment component containing at least two linking domains and the compound supplying the anchoring moiety component, can be supplied in a package which contains instructions for forming the multicomponent complex of the invention.

In another embodiment of the invention, at least two of the compounds necessary for forming the multicomponent complex of the invention, the compound supplying the bioeffecting domain component, the compound supplying the segment component containing at least two linking domains and the compound supplying the anchoring moiety component, can be supplied in a container which contains instructions for forming the multicomponent complex of the invention.

In yet another embodiment of the invention, at least three of the compounds necessary for forming the multicomponent complex of the invention, the compound supplying the bioeffecting domain component, the compound supplying the segment component containing at least two linking domains and the compound supplying the anchoring moiety component, can be supplied in a container which contains instructions for forming the multicomponent complex of the invention.

In another aspect of the invention, the invention may be used in methods of delivering bioeffecting agents to particular locations. A bioeffecting agent can be attached to a substrate with a multicomponent complex of the invention by any of the methods described. The substrate is then placed in the location in which it is desired to deliver the bioeffecting agent. After placement of the substrate delivering the bioeffecting agent, disassociation of the cleavable linkage begins to occur, and the release of the bioeffecting agent in the area surrounding the substrate begins to occur. The rate of release will be affected by the conditions in the local environment, e.g. temperature, moisture and pH.

When delivering bioeffecting agents in vivo in animals or humans the substrate is in the form of an article capable of providing adequate support and surface area for the delivery of the bioeffecting agent. The size and shape of the article will vary depending on the method of delivery being used and the desired role of the bioeffecting agent.

For example, a stent may be coated with compositions containing the multicomponent complex of the invention. The stent may be placed on a catheter which can be threaded through the human vasculature until a desired location is reached. The stent may be removed from the catheter and may be retained in the desired location for some period of time. In the moist environment of the vasculature, hydrolysis reactions will begin to release the bioeffecting agent into the area surrounding the stent. Bioeffecting agents delivered locally can be very effective in treating a range of disease states and conditions. It is often possible to obtain the desired effect using a very small amount of the bioeffecting agent, because it is being targeted to the desired area. Local delivery also avoids the systemic effects which often result when agents are delivered by traditional routes, such as ingestion and injection. For example, when heparin is delivered to a particular site in the vasculature, its antithrombogenic and antiproliferative effects can be realized in a desired location without causing the systemic "blood thinning" caused when heparin is administered by other routes.

The articles used to deliver bioeffecting agents can take a variety of forms. A polymer can be used to occlude an artery. A bioeffecting agent with antibacterial properties can be absorbed into the polymer using a multicomponent complex of the invention. The antibacterial agent will be slowly released and will prevent infection at the site of occlusion. Delivery of the antibacterial agent in this manner allows the use of advantageous lower doses of bioeffecting agents and potentially avoids systemic effects, such as the opportunistic fungal infections which often result from lengthy courses of antibiotic treatment.

The invention is further illustrated by the following non-limiting examples. The contents of all the references cited throughout this application are expressly incorporated by reference.

EXAMPLE 1

Preparation of a Sustained Release Antimicrobial Coating

The following components are combined in the order listed:

100 parts by weight UE 40-439

10 parts by weight protargen (silver protein)

5 parts by weight KM10-1610 (leveling/flow aid)

5 parts by weight KM10-1703 (linker)

(UE 40-439, KM10-1610, and KM10-1703 can be purchased from Stahl of Peabody, Mass.)

After mixing with good agitation, the mixture is allowed to stand for 30 minutes. The mixture can then be applied to the surface of a standard vinyl bath mat until a 3.0 mil thick coating is obtained. The coating will inhibit microbial growth, both bacterial and fungal.

EXAMPLE 2

Preparation of a Sustained Release Antimicrobial Resin

The following components are combined in the order listed:

5 parts by weight nystatin (Mycostatin)

5 parts by weight protargen (silver protein)

5 parts by weight KM10-1703 (linker)

pigment and stabilizers are optional additions (KM 10-1703 can be purchased from Stahl of Peabody, Mass. and Mycostatin can be purchased from Bristol Myers Squibb)

After mixing with good agitation, the dry mixture is added to 100 parts of a dry blend of vinyl resin containing a small amount of acid functional vinyl resin. (A pre-mill of the dry blend of the vinyl composition may be dictated.) The vinyl resin should be milled according to standard roll manufacturing with minimal heat history.

A flexible vinyl film formulation containing standard weights of vinyl resin forms. A multicomponent complex of the invention also forms, which attaches the bioeffecting agents containing antimicrobial and antifungal properties to the vinyl resin. The vinyl composite film formed is useful for items such as bath mats and shower curtains.

EXAMPLE 3

Comparison of the Binding Stability of the Sodium and Ammonium Salts of Heparin

Ammonium heparin was purchased from Celsus Labs. Sodium heparin and toluidine blue O were purchased from Aldrich. MichemPrime 4983R was purchased from Michelman. KM10-1703 was purchased from Stahl of Peabody, Mass.

Two solutions, each containing 2% solids of sodium heparin and ammonium heparin in a 50/50 blend of water and isopropanol were prepared. One glass slide was dipcoated in the solution containing sodium heparin, and another glass slide was dipcoated in the solution containing the ammonium heparin.

An emulsion of MichemPrime 4983R (acrylic polymer) was diluted to a 50/50 weight ratio and added to the heparin solutions. An excess of KM 10-1073 (linker) was also added to each solution. One glass slide was dipcoated in the solution containing sodium heparin/acrylic, and another glass slide was dipcoated in the solution containing the ammonium heparin/acrylic.

The binding stability of heparin to the glass substrate was evaluated by staining in a 2% solution of toluidine blue O, rubbing and rinsing the slides:

| Sample No. | Compound | Binding Stability | Stain Intensity |
|---|---|---|---|
| 3-176 A | Ammonium Heparin | removes w/rubs | strong |
| 3-176 B | Ammonium Heparin/ Linker/Binder | persists w/10 rubs | faint |
| 3-176 G | Sodium Heparin | removes w/falling water | strong |
| 3-176 F | Sodium Heparin/ Linker/Binder | removes with rubs | faint |

In selecting a heparin additive, sodium heparin salts are generally chosen due to the ability of the body to easily handle sodium e.g. isotonic saline is based on sodium chloride. The sodium counter-ion is naturally occurring and biologically a known quantity. However, the sodium salt of heparin, while a bioeffecting agent, does not contain a bioeffecting domain component and cannot form a cleavable linkage with a linking domain. The ammonium salt of heparin, however, naturally contains a bioeffecting domain component. Therefore, this experiment demonstrated that an ammonium heparin salt attached to a substrate with a multicomponent complex of the invention is released more slowly than either sodium heparin or ammonium heparin attached in another manner.

EXAMPLE 4

Assessment of Binding Stability of Ammonium Heparin Salt with Various Linker Compounds Ammonium heparin was purchased from Celsus Labs. Toluidine blue O dye was purchased from Aldrich. KM10-1703 was purchased from Stahl of Peabody, Mass. Tyzor AA was purchased from Dupont of Wilmington, Del. Cymer 303 was purchased from Cytec, New Jersey. Epi-rez-5522-WY-55 was purchased from Shell Chemical, Texas.

A solution containing 2% solids of ammonium heparin in a 50/50 blend of water and isopropanol was prepared. Solutions containing samples of KM-1703 (linker), Tyzor AA (titanite), and Cymer 303 (melamine-formaldehyde), and Epi-rez 5522-WY-55 (epoxy) were added to aliquots of the ammonium heparin solution. One glass slide was dip-coated in each solution.

The binding stability of heparin to the glass substrate was evaluated by staining in 2% solution of toluidine blue O, rubbing and rinsing the slides:

| Sample | | Binding/Stability | Stain Intensity |
|---|---|---|---|
| 3-176 C | ammonium heparin/aziridine | stays w/10 rubs | moderate |
| 3-176 D | ammonium heparin/titanate | removes with rubs more persistent than 3-176A | strong |
| 3-176 E | ammonium heparin/melamine | stays w/10 rubs | moderate |
| 3-176 H | ammonium heparin/epoxy | removes with rubs more persistent than 3-176A | moderate |
| 3-176 A | ammonium heparin/none | removes with rubs | strong |
| 3-176 G | sodium heparin/none | removes with falling water | strong |

After being soaked for 24 hours in water, all the samples maintained a level of stain color similar to the level of stain color before soaking. The aziridine and the melamine linked complexes appeared to be the most durable of the compounds tested, but all compounds tested demonstrated an improvement over the control samples.

EXAMPLE 5

Experimental Comparison of the Rate of Release of a Protein Bioeffecting Agent Triton X-100 was purchased from Rohm & Hass, Pennsylvania. BSA was obtained from the Chemistry Department, University of Lowell. MichemPrime 4983R was purchased from Michelman. KM10-1703 was purchased from Stahl of Peabody, Mass.

Approximately 1% Triton X-100 (a nonionic surfactant) was added to a solution of fluorescamine labelled bovine serum albumin (BSA). An emulsion of MichemPrime 4983R (acrylic polymer) was diluted to 15% solids in water by weight. A solution containing 10% solids in water by weight of KM 10-1703 was also prepared.

Four glass slides were dipped into the acrylic emulsion, and the excess emulsion was allowed to drain from the slide for 5 minutes. The slides were then dried at 150° F. for 15 minutes. Two of the slides were soaked for 5 minutes in the KM10-1703 solution. These slides were then dried at ambient temperature for 15 minutes. One drop of the labelled BSA solution was added to each side of all 4 slides. The slides were allowed to dry at ambient temperature overnight. After drying, the slides were soaked for 15 minutes in water at 37° C. and then examined.

Under ultraviolet light, the coating on the slides treated with the KM 10-1703 solution appeared to glow, indicating the continued presence of BSA. These slides appeared hazy under normal lighting conditions. The slides not treated with the KM 10-1703 solution showed no changes under either lighting condition, indicating no labeled BSA remained. The appearance of both sets of slides was unchanged after the second soaking period.

The fluorescamine labeling chemical/technique used in this example binds the amine functionality on the BSA protein chain, leaving the acid functions available for reaction. This labeling technique is routinely used to observe the spectrophotometric/chromatographic separation of proteins. The results obtained in this experiment demonstrated that the release of a protein (BSA), attached to a substrate with a multicomponent complex of the present invention was sustained over time, in comparison to the same protein attached to the same substrate attached in an alternate manner.

EXAMPLE 6

Rate of Heparin Release from a Substrate (Two-step Application Method)

R-9603 was purchased from Zeneca Resins, Wilmington, Mass. Povidone 90 was purchased from ISP Chemicals, New Jersey. KM 10-1703 was purchased from Stahl, Peabody, Mass. Ammonium and benzalkonium heparin were purchased from Celsus Labs. Distilled water was purchased from Poland Springs, Me.

A first urethane solution was prepared by dissolving 150.0 g R-9603, 16.8 g PVP and 3.0 g KM10-1703 in 87.35 g distilled water. A second urethane solution was prepared by dissolving 150.0 g R-9603, 16.8 g PVP and 4.5 g KM10-1703 in 87.35 g distilled water. Dried films were prepared that were approximately 3.0 mils thick. A 2% by weight ammonium heparin solution was also prepared.

The three samples were coated as follows:

3-145-2 Dried film of first urethane solution; post-dipped in benzalkonium chloride salt of heparin.

3-146-7 Dried film of first urethane solution; post-dipped in ammonium heparin solution.

3-145-4 Dried film of second urethane solution; post-dipped in ammonium heparin solution.

Coating squares 1.0 cm per side in size were prepared by casting aqueous dispersions of urethane containing a hydrophilic polymer and heparin. After soaking the coating squares for 1 hour in a 0.9% aqueous saline solution, a sample was taken and the saline solution changed. In the same manner, the soaking solutions were removed, and fresh saline added to containers containing the squares after 12 hours and at 1, 4, 5, 6, 7, 10 and 14 days. (The purpose of this flushing was to mimic the continual flushing of residual bioeffecting material from the site of use by blood, urine or other passing fluids.)

A pooled human plasma sample was used to obtain partial thromboplastin times (PTT). Various dilutions of the samples were used to determine the ranges for maximum sensitivity per sample. Measurements were taken in seconds and times of approximately 70–150 seconds were sought. Back-calculating through the dilutions provided the actual levels of release.

Figure 6:
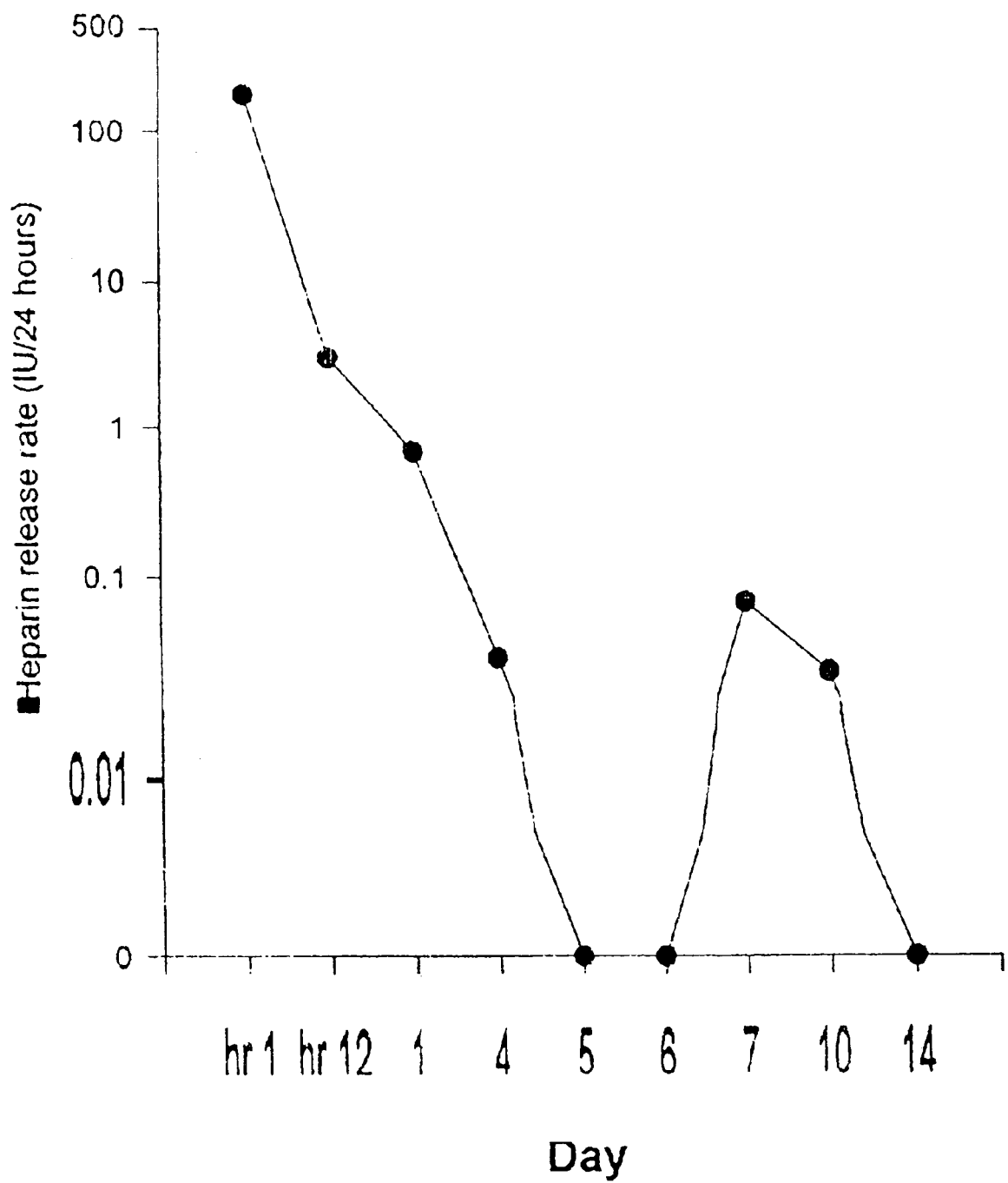
FIG. 6 is a graphic representation of the rate of heparin release from a polyurethane film post-coated with a standard benzalkonium heparin. (3-145-2)

As can be seen from the graphs of FIGS. 6–8, the release of heparin from a coating square one cm in size and approximately 3.0 mils thick occurs as follows:

FIG. 6—3-145-2 Control/standard coating.

Release of therapeutic amounts of heparin; less than 1.0 IU is lost at 0.75 days.

Figure 7:
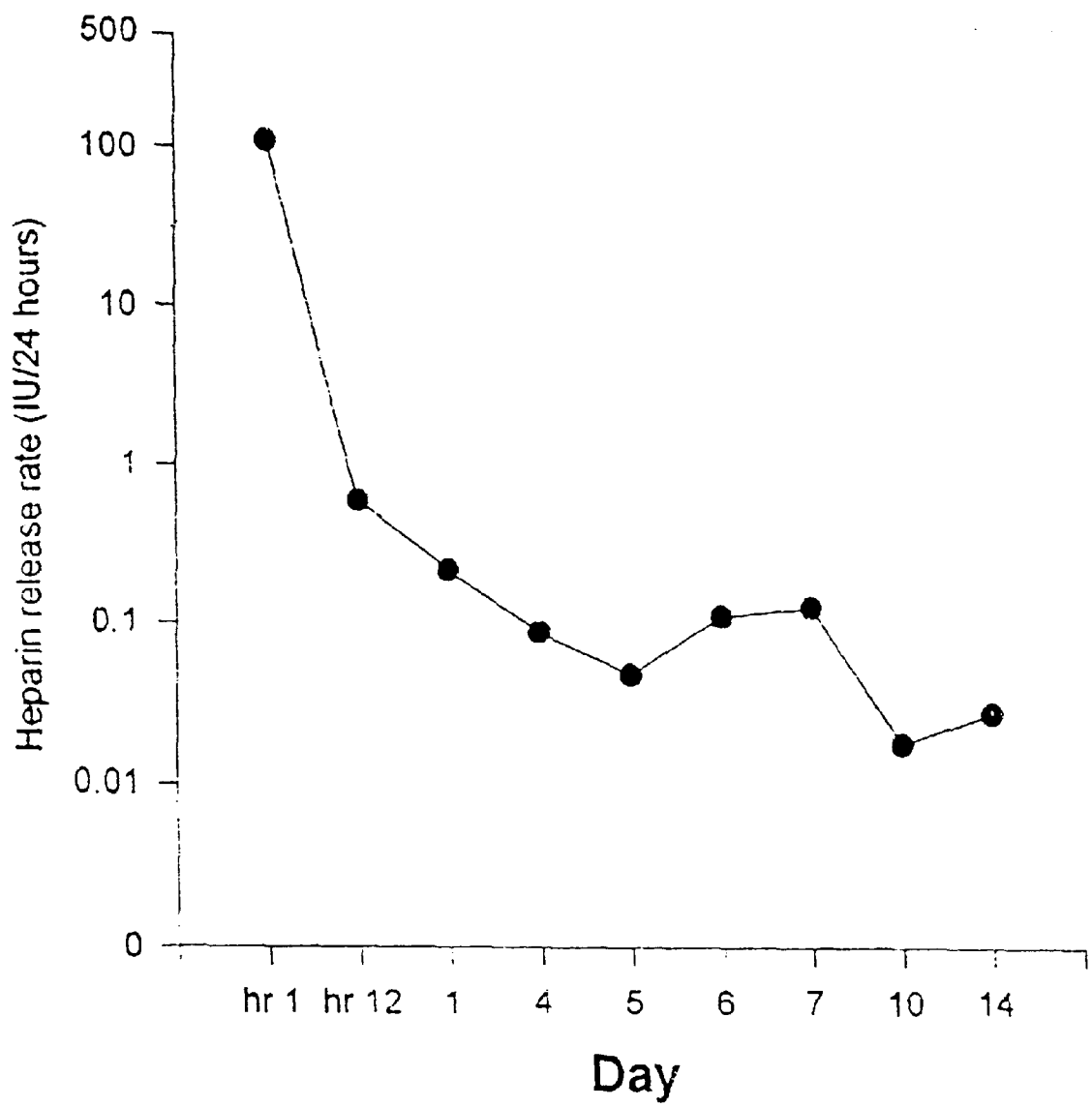
FIG. 7 is a graphic representation of the rate of heparin release from a polyurethane film created with a solution of aqueous ammonium heparin. (3-146-7)
Figure 8:
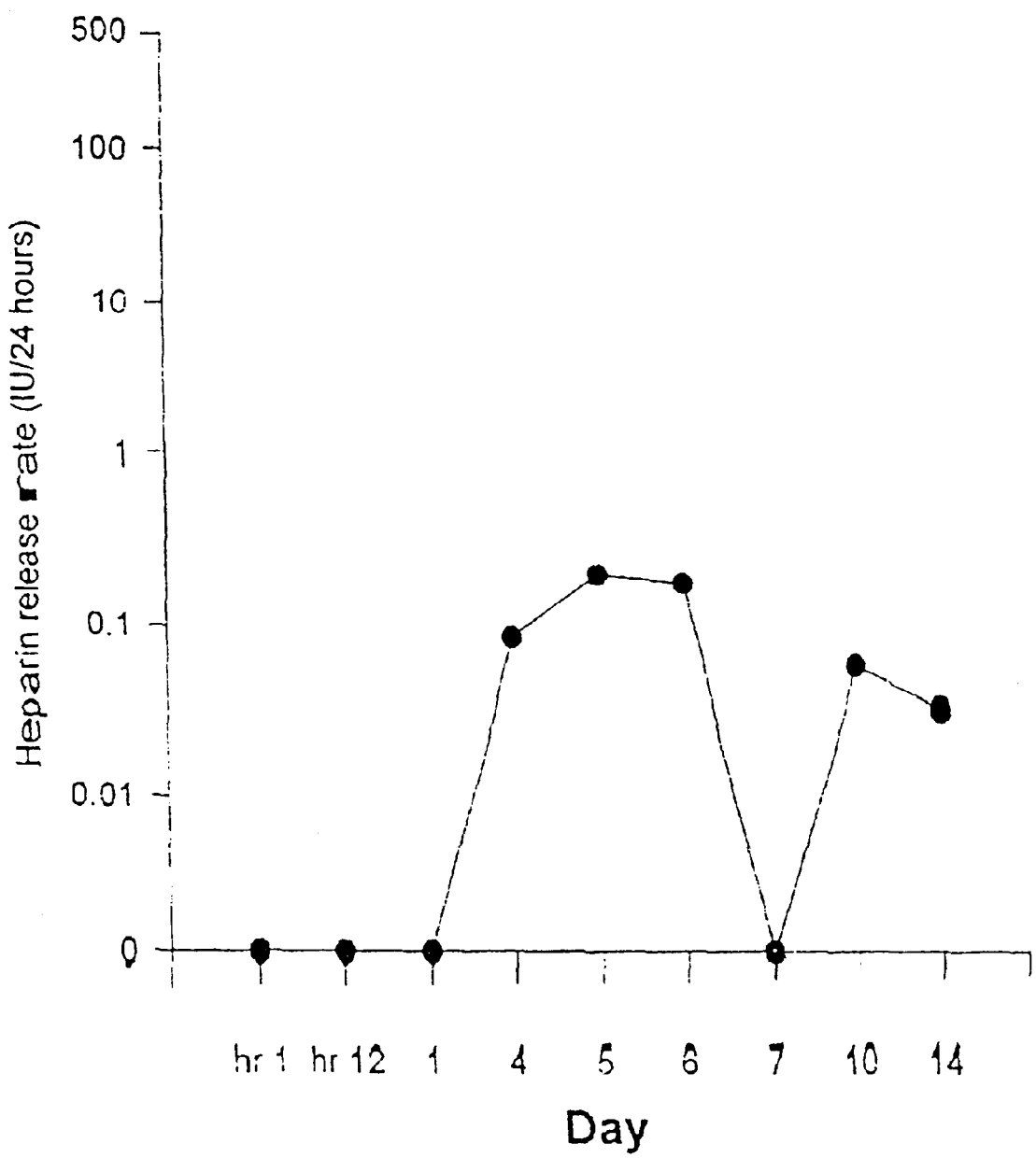
FIG. 8 is a graphic representation of the rate of release of heparin attached with a multi-component complex of the invention from a polyurethane film created with a solution of aqueous ammonium heparin. (3-146-4)

FIG. 7—3-146-7 Coating without multicomponent complex. Release was inconsistent; no therapeutic level observed at any time.

FIG. 8—3-145-4 Coating with multicomponent complex.

Release was significantly more uniform and prolonged with some activity maintained at a low level at two weeks. Therapeutic levels were lost at 0.5 days similar to the benzalkonium salt.

These results demonstrate the improvement in the rate of release for heparin attached with a multicomponent complex of the invention, when compared to ammonium heparin without attachment (first urethane solution).

EXAMPLE 7

Rate of Heparin Release from a Hydrophilic Substrate (One-step Application Method)

R-9603 was purchased from Zeneca Resins, Wilmington, Mass. Povidone 90 was purchases from ISP Chemicals, New Jersey. KM 10-1703 was purchased from Stahl, Peabody, Mass. Ammonium and benzalkonium heparin were purchased from Celsus Labs. Distilled water was purchased from Poland Springs, Me.

As in Example 6, the first urethane solution was prepared by dissolving 150.0 g R-9603, 16.8 g PVP and 3.0 g KM10-1703 in 87.35 g distilled water. Dried films were prepared that were approximately 3.0 mils thick.

3-145-2 Dried film of first urethane solution; post-dipped in benzalkonium chloride salt of heparin.

A se con d urethane solution was prepared by dissolving 150.0 g R-9603 and 16.8 g PVP in 87.35 g distilled water. 10% by weight ammonium heparin was added to the solution and allowed to dissolve.

A third urethane solution was prepared by dissolving 150.0 g R-9603, 16.8 g PVP and 4.5 gKM10-1703 in 87.35 g distilled water. 10% by weight ammonium heparin was added to the solution and allowed to dissolve.

Dried films of the second urethane solution (3-146-9) and the third urethane solution (3-146-5) were prepared th at were approximately 3.0 mils thick.

Coating squares 1.0 cm per side in size we re prepared by casting aqueous dispersions of urethane containing a hydrophilic polymer and heparin. After soaking the coating squares for 1 hour in a 0.9% aqueous saline solution, a sample was taken and the saline solution changed. In the same manner, the soaking solutions were removed, and fresh saline added to containers containing the squares after 12 hours and at 1, 4, 5, 6, 7, 10 and 14 days. (The purpose of this flushing was to mimic the continual flushing of residual bioeffecting material from the site of use by blood, urine or other passing fluid.) A pooled human plasma sample was used to obtain partial thromboplastin times (PTT). Various dilutions of the samples were used to determine the ranges for maximum sensitivity per sample. Measurements were taken in seconds and times of approximately 70–150 seconds were sought. Back-calculating through the dilutions provided the actual levels of release.

(By way of reference, experience indicates that day five after stenting appears to be the worst for thrombosis. Therefore, the critical release of an anticoagulant in the vicinity of a stent should be measurable (i.e. above a rate of 1.0 IU/24 hour) for the four (4) preceding days. After that there is initial indication that the prolonged release of heparin and/or other bioeffecting cell growth regulators can impact the proliferative response to reduce the reclosure, restenosis and/or damage to the surrounding cells which often follows arterial trauma.)

As can be seen from the graphs of FIGS. 6, 9 & 10, the release of heparin from a coating square one cm in size and approximately 3.0 mils thick occurs as follows:

FIG. 6—3-145-2 Control/standard coating. Release of therapeutic amounts of heparin; less than 1.0 IU is lost at 0.75 days.

Figure 9:
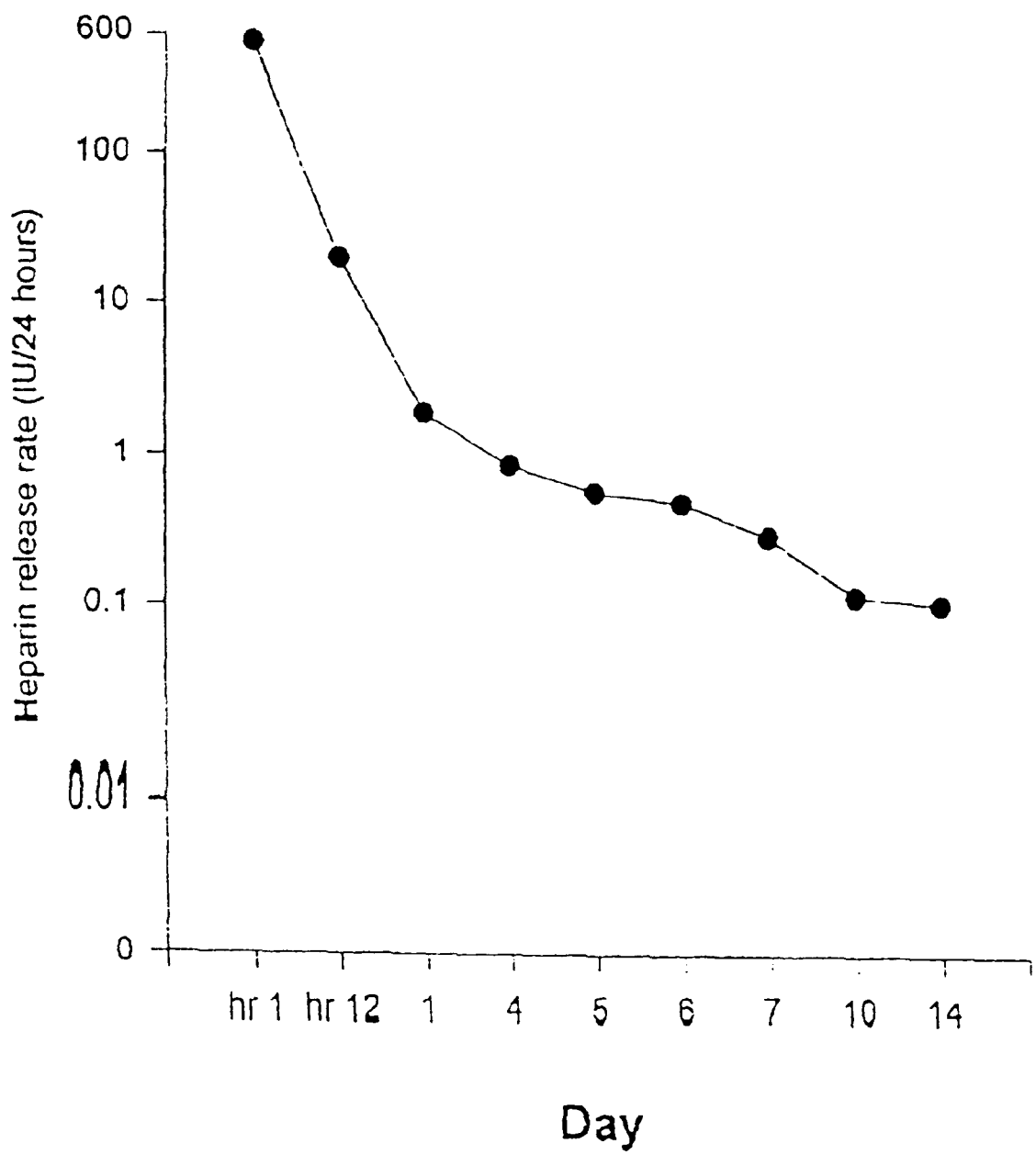
FIG. 9 is a graphic representation of the rate of heparin release from a hydrophilic film of a polyurethane resin. (3-146-9)
Figure 10:
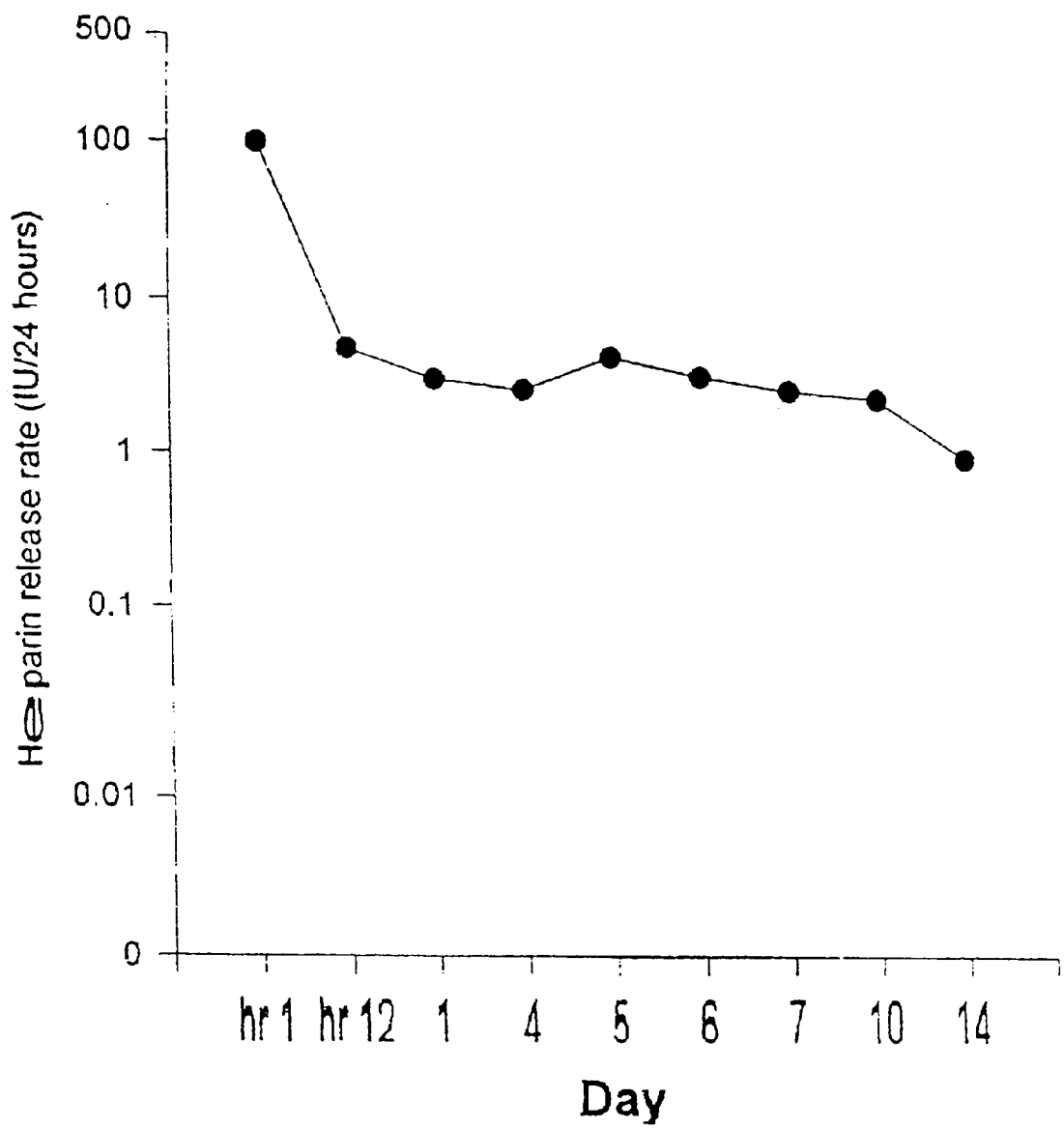
FIG. 10 is a graphic representation of the rate of release of heparin attached with a multi-component complex of the invention from a hydrophilic polyurethane film. (3-146-5)

FIG. 9—3-146-9 Hydrophilic coating without multicomponent complex. Showed initially strong release above 1.0 IU/24 hr. Therapeutic levels lost at day 1. Some lower and declining activity was maintained at measurable levels through day 14.

FIG. 10—3-146-5 Hydrophilic coating with multicomponent complex. Therapeutic levels maintained throughout the test. A fairly straight line level amount was released at 1.0 IU for the period between 1–14 days. Only slight loss in activity over 14 days.

These results additionally demonstrate the improvement in sustained release for the heparin sample attached to the substrate with a multicomponent complex of the invention.

EXAMPLE 8

Modification of a Bioeffecting Agent

A reaction product of aliphatic isophorone diisocyanate (IPDI) with dimethylolpropionic acid (DMPA) is prepared by reaction under nitrogen purge at 100° C. for 4 hours, of 2 equivalents of isocyanate groups from IPDI with 1 equivalent of DMPA hydroxyl groups. Due to the differential reactivity of the isocyanate groups on IPDI, there is large amount of isocyanate-"capped" DMPA. A titration of the isocyanate functionality yields the % available NCO for reaction with the amine function on silver sulfadiazine (SSD). The isocyanate functional product is then added to 2 equivalents (calculated from the % isocyanate of the titration by standard backtitration of dibutyl amine with hydrochloric acid) of amine functional silver sulfadiazine and the amine/NCO reaction should proceed rapidly with some exotherm.

The resulting acid functional derivative of SSD is neutralized with ammonia and used in preparation of a coating product as in Examples 6 or 7. A coating prepared in this manner would exhibit prolonged antimicrobial activity.

EXAMPLE 9

Difunctional Spacer

A polymer surface is primed with a solution of acid containing polymer (MichemPrime 4983R, Michelman) and allowed to dry. The surface is washed with a ten percent (10%) aqueous solution of Waterpoxy 1401 (Henkel Corporation) polyfunctional epoxy and baked thirty (30) minutes at 150° C. to dry. Within four hours, the samples are immersed in a C-8 terminal-acid/amine functional 8-aminocaprylic acid solution and allowed to remain for 15 minutes. The sample is removed and dried 30 minutes at 100° C. After rinsing in running water to remove any unreacted caprylic acid, the sample is immersed in a premixed, aged solution of the reaction product of 3 imine equivalents of KM10-1703 reacted with 1 equivalent of acid function of nystatin (Mycostatin Bristol, Myers, Squibb). The resulting layered structure allows more availability of the nystatin to its environment and an increased exposure to the hydrolytic degradation if that environment.

EXAMPLE 10

Arterial Occluder with Reversibly Attached Bioeffecting Agents

Using the method described below, an artery which provides a blood supply to a tumor can be injected with a swellable polyvinyl alcohol (PVA) in its dried, flake form. The PVA quickly expands and occludes the lumen of the artery. PVA flakes (Cook, Inc., Bloomington, Ind.) are expanded into a solution of aqueous multicomponent complex which is isocyanate functional. PVA contains a reactive-OH (hydroxyl) group.

A reactive pre-polymer (Desmodur N-100, Bayer Corp., Pittsburgh, Pa.) is pre-reacted with a 0.5 stoichiometric (consuming 0.5 equivalents of the NCO groups with the OH groups) amount of dimethylolpropionic acid (DMPA). All the acid functionality on the DMPA is reacted (1.0 equivalents) with three times (3.0 equivalents) of a linking agent (KM10-1703, Stahl, Peabody, Mass.). A growth regulator e.g. Ferrochrome A, and chemotherapeutic agents e.g. 6-thioguanine (Glaxo Wellcome) can be attached to the resulting linking domains in the desired ratio, with a stoichiometric amount of acid groups on the bioactive agent for the available linking domains.

The above reaction product exhibits an isocyanate functionality, which can be verified by IR and quantified by standard dibutyl amine/hydrochloric acid back titration of isocyanates. It is then dispersed into water at approximately 10% solids or less. If necessary surfactants and cosolvents can be added to improve the dispersibility or ptake by the PVA flakes.

Finally, the PVA flake is added and swollen in the aqueous mixture, cured at 70° C. overnight and vacuum dried. The subsequent product shows good activity of the bioeffecting agent, with little effect on the function of the flakes.

Those skilled in the art will recognize, or be able to ascertain using no more than routine experimentation, numerous equivalents to the specific embodiments described herein. Such equivalents are considered to be within the scope of this invention and are covered by the following claims.

What is claimed is:

1. The combination of a multicomponent complex for delivering a bioeffecting agent for use with a substrate and an article, comprising a first complex for use with a substrate and for delivering a bioeffecting agent having the following formula:

[Q]-[S]-[T]

wherein Q is a bioeffecting domain component;

S is a segment component containing at least two linking domains; and

T is an anchoring moiety component, the components selected such that a cleavable linkage anchored to the substrate is formed which sustains the release of the bioeffecting agent over time, and a second article in contact with the first complex.

2. The combination of claim 1 wherein the bioeffecting domain component is supplied by a compound which has a property selected from the group consisting of agents with antithrombogenic, antimicrobial, antiinflammatory, analgesic, and cell growth properties.

3. The combination of claim 2 wherein the agent is a heparin compound.

4. The combination of claim 3 wherein the heparin compound is ammonium heparin.

5. The combination of claim 1 wherein the bioeffecting domain component is supplied by a compound selected from the group consisting of vitamins, mineral complexes, proteins and enzymes.

6. The combination of claim 5 wherein the bioeffecting domain component is supplied by a compound which is a cell growth factor.

7. The combination of claim 1 wherein the cleavable linkage is an ester.

8. The combination of claim 1 wherein the segment component is supplied by a compound selected from the group consisting of aziridines, epoxys, formaldehydes and metal esters.

9. The combination of claim 8 wherein the segment component is supplied by an aziridine.

10. The combination of claim 1 wherein the article is a medical device.

11. The combination of claim 10 wherein the medical device is adapted for in vivo uses.

12. A multicomponent complex for delivering a bioeffecting agent for use with a substrate having the following formula:

[Q]-[S]-[T]

wherein Q is a bioeffecting domain component;

S is a segment component containing at least two linking domains; and

T is an anchoring moiety component, the components selected such that a cleavable linkage anchored to the substrate is formed which sustains the release of the bioeffecting agent over time.

13. The complex of claim 12 wherein the bioeffecting domain component is supplied by a compound with a property selected from the group consisting of agents with antithrombogenic, antimicrobial, antiinflammatory, analgesic, and cell growth properties.

14. The complex of claim 13 wherein the agent is a heparin compound.

15. The complex of claim 14 wherein the heparin compound is ammonium heparin.

16. The complex of claim 12 wherein the bioeffecting domain component is supplied by a compound selected from the group consisting of vitamins, mineral complexes, proteins and enzymes.

17. The complex of claim 16 wherein the bioeffecting domain component is supplied by a growth factor.

18. The complex of claim 12 wherein the cleavable linkage is an ester.

19. The complex of claim 12 wherein the segment component is supplied by a compound selected from the group consisting of aziridines, epoxys, formaldehydes and metal esters.

20. The complex of claim 19 wherein the segment component is supplied by an aziridine.

21. The complex of claim 12 wherein the anchoring moiety component is supplied by a urethane.

22. The complex of claim 12 wherein the substrate is a medical device.

23. The complex of claim 22 wherein the medical device is adapted for in vivo uses.

24. A composition for delivering a bioeffecting agent for use with a substrate comprising:

a first complex for use with a substrate and for delivering a bioeffecting agent having the following formula:

[Q]-[S]-[T]

wherein Q is a bioeffecting domain component;

S is a segment component containing at least two linking domains; and

T is an anchoring moiety component, the components selected such that a cleavable linkage anchored to the substrate is formed which sustains the release of the bioeffecting agent over time, and a second solution in contact with the first complex.

25. The composition of claim 24 wherein the compounds supplying Q, S and T are provided in a container as a single component.

26. The composition of claim 24 wherein the compounds supplying Q, S and T are provided as two components.

27. The composition of claim 24 wherein the compounds supplying Q, S and T are provided as three components.

28. The composition of any of claims 25, 26 or 27 wherein Q is supplied by a compound with a property selected from the group consisting of pharmaceuticals with antithrombogenic, antimicrobial, antiinflammatory, analgesic, and cell growth properties.

29. The composition of claim 28 wherein the pharmaceutical is a heparin compound.

30. The composition of claim 29 wherein the heparin compound is ammonium heparin.

31. The composition of any of claims 25, 26 or 27 wherein Q is supplied by a compound selected from the group consisting of vitamins, mineral complexes, proteins and enzymes.

32. The composition of claim 31 wherein Q is supplied by a growth factor.

33. The composition of any of claims 25, 26 or 27 further comprising a hydrophilic agent.

34. The composition of any of claims 25, 26 or 27 wherein the cleavable linkage is an ester.

35. The composition of any of claims 25, 26 or 27 wherein S is supplied by a compound selected from the group consisting of aziridines, epoxys, formaldehydes and metal esters.

36. The composition of claim 35 wherein S is supplied by an aziridine.

37. The composition of any of claims 25, 26 or 27 wherein the anchoring moiety component is supplied by a urethane.

38. The complex of any of claims 25, 26 or 27 wherein the substrate is a medical device.

39. The complex of claim 38 wherein the medical device is adapted for in vivo uses.

40. A packaged composition for delivering a bioeffecting agent for use with a substrate comprising:

a container holding a compound supplying at least one component of a multicomponent complex having the following formula:

[Q]-[S]-[T]

wherein Q is a bioeffecting domain component;

S is a segment component containing at least two linking domains; and

T is an anchoring moiety component, the components selected such that a cleavable linkage anchored to the substrate is formed which sustains the release of the bioeffecting agent over time, and instructions for using the composition for delivering a bioeffecting agent.

41. The packaged composition of claim 40 wherein the compound supplying Q is contained in the package.

42. The packaged composition of claim 40 wherein the compound supplying S is contained in the package.

43. The packaged composition of claim 40 wherein the compound supplying T is contained in the package.

44. The packaged composition of claim 40 wherein the bioeffecting domain component is supplied by a compound with a property selected from the group consisting of agents with antithrombogenic, antimicrobial, antiinflammatory, analgesic, and cell growth properties.

45. The packaged composition of claim 44 wherein the agent is a heparin compound.

46. The packaged composition of claim 45 wherein the heparin compound is ammonium heparin.

47. The packaged composition of claim 40 wherein the bioeffecting domain component is supplied by a compound selected from the group consisting of vitamins, mineral complexes, proteins and enzymes.

48. The packaged composition of claim 40 wherein the bioeffecting domain component is supplied by a growth factor.

49. The packaged composition of claim 40 wherein the cleavable linkage is an ester.

50. The packaged composition of claim 40 wherein the segment component is supplied by a compound selected from the group consisting of aziridines, epoxys, formaldehydes and metal esters.

51. The packaged composition of claim 40 wherein the segment component is supplied by an aziridine.

52. The packaged composition of claim 40 wherein the anchoring moiety component is supplied by a urethane.

53. The packaged composition of claim 40 wherein the substrate is a medical device.

54. The packaged composition of claim 53 wherein the medical device is adapted for in vivo uses.

55. A method for providing a sustained release bioeffecting coating on the surface of an article, the method comprising:

applying a coating solution to a surface of the article such that a layer containing the sustained release bioeffecting coating is formed upon the article surface, wherein the formed layer contains a multicomponent complex containing a bioeffecting domain component, a segment component containing at least two linking domains, and an anchoring moiety component, the components selected such that a cleavable linkage anchored to the substrate is formed, and the release of the bioeffecting domain is sustained over time.

56. The method of claim 55 wherein the bioeffecting domain component is supplied by a compound with a property selected from the group consisting of agents with antithrombogenic, antimicrobial, antiinflammatory, analgesic, and cell growth properties.

57. The method of claim 56 wherein the agent is a heparin compound.

58. The method of claim 57 wherein the heparin compound is ammonium heparin.

59. The method of claim 55 wherein the bioeffecting domain component is supplied by a compound selected from the group consisting of vitamins, mineral complexes, proteins and enzymes.

60. The method of claim 59 wherein the bioeffecting domain component is supplied by a growth factor.

61. The method of claim 55 wherein the coating solution contains a hydrophilic agent.

62. The method of claim 55 wherein the cleavable linkage is an ester.

63. The method of claim 55 wherein the segment component is supplied by a compound selected from the group consisting of aziridines, epoxys, formaldehydes and metal esters.

64. The method of claim 63 wherein the segment component is supplied by an aziridine.

65. The method of claim 55 wherein the article is a medical device.

66. The method of claim 55 wherein the medical device is adapted for in vivo uses.

* * * * *